(12) United States Patent
Reiner (10) Patent No.: US 7,831,445 B2
(45) Date of Patent: Nov. 9, 2010

(54) METHOD AND APPARATUS FOR GENERATING AN ADMINISTRATIVE QUALITY ASSURANCE SCORECARD

(76) Inventor: Bruce Reiner, 6 Greenleaf La., Seaford, DE (US) 19973

( * ) Notice: Subject to any disclaimer, the term of this patent is extended or adjusted under 35 U.S.C. 154(b) by 954 days.

(21) Appl. No.: 11/699,350

(22) Filed: Jan. 30, 2007

(65) Prior Publication Data

US 2007/0179811 A1  Aug. 2, 2007

Related U.S. Application Data

(60) Provisional application No. 60/762,859, filed on Jan. 30, 2006, provisional application No. 60/763,353, filed on Jan. 31, 2006, provisional application No. 60/763,357, filed on Jan. 31, 2006, provisional application No. 60/771,482, filed on Feb. 9, 2006, provisional application No. 60/771,484, filed on Feb. 9, 2006.

(51) Int. Cl.
  *G06Q 10/00* (2006.01)
  *G06Q 50/00* (2006.01)
(52) U.S. Cl. .................... 705/2; 705/3; 705/7
(58) Field of Classification Search ............... 705/2–3, 705/7, 10
See application file for complete search history.

(56) References Cited

U.S. PATENT DOCUMENTS

| | | |
|---|---|---|
| 2003/0212580 A1 | 11/2003 | Shen |
| 2004/0078236 A1* | 4/2004 | Stoodley et al. ............... 705/2 |
| 2005/0203775 A1 | 9/2005 | Chesbrough |
| 2005/0251013 A1* | 11/2005 | Krishnan et al. ............ 600/407 |
| 2007/0179805 A1* | 8/2007 | Gilbert et al. .................. 705/2 |

* cited by examiner

*Primary Examiner*—Luke Gilligan
(74) *Attorney, Agent, or Firm*—Jean C. Edwards, Esq.; Akerman Senterfitt

(57) ABSTRACT

The present invention provides a quality assurance system and method that generates a quality assurance (QA) scorecard for administrators that oversee use of digital devices in a radiological-based medical imaging study. According to one embodiment, client computers, servers, imaging devices, databases, and/or other components may be coupled to provided a unified data collection system. According to one embodiment, systems and methods are provided that analyze various parameters that are derived from the unified data collection system to calculate a QA score for analysis by administrators. The QA score provides a combined subjective and objective feedback system that includes performance evaluations from other users, including clinicians, radiologists, technologists and patients. According to one embodiment, the feedback may be provided in real-time.

23 Claims, 3 Drawing Sheets

FIGURE 3

METHOD AND APPARATUS FOR GENERATING AN ADMINISTRATIVE QUALITY ASSURANCE SCORECARD

CROSS-REFERENCE TO RELATED APPLICATIONS

This application claims priority from U.S. Provisional Patent Application No. 60/762,859, dated Jan. 30, 2006, U.S. Provisional Patent Application No. 60/763,353, dated Jan. 31, 2006, U.S. Provisional Patent Application No. 60/763,357, dated Jan. 31, 2006, U.S. Provisional Patent Application No. 60/771,482, dated Feb. 9, 2006, U.S. Provisional Patent Application No. 60/771,484, dated Feb. 9, 2006, the contents of which are herein incorporated by reference in their entirety.

This application is related to the following concurrently filed commonly owned U.S. patent applications entitled, "Method And Apparatus For Generating A Technologist Quality Assurance Scorecard" Ser. No. 11/699,348 filed Jan. 30, 2007; "Method And Apparatus For Generating A Patient Quality Assurance Scorecard" Ser. No. 11/699,349 filed Jan. 30, 2007; "Method And Apparatus For Generating A Radiologist Quality Assurance Scorecard" Ser. No. 11/699,344 filed Jan. 30, 2007; and "Method And Apparatus For Generating A Clinician Quality Assurance Scorecard" Ser. No. 11/699,351 filed Jan. 30, 2007, the contents of all of which are herein incorporated by reference in their entirety.

BACKGROUND OF THE INVENTION

1. Field of the Invention

The present invention relates to a quality assurance (QA) system and method that quantitatively rates users that perform and/or participate in medical procedures, particularly in the area of radiology. The present invention relates to systems, methods and computer-based software programs that analyze data and generate QA scorecards for administrators. In the process of doing so, a number of objective data are collected for real-time and future analysis, thereby providing objective feedback to administrators for continuing quality improvement. In the end, the invention is intended to improve patient safety and overall clinical outcomes.

2. Description of the Related Art

The first and foremost priority for any QA program is to improve quality of service. As QA programs are implemented in the medical field, the ultimate goal is to improve patient care. To accomplish this goal, products and/or services should offer procedures for increasing accountability and improving feedback among users that participate in a medical study. This ultimately will enhance patient diagnosis and/or treatment, which leads to objective improvements in overall health outcomes.

Medical imaging has undergone a transition from film-based imaging technologies to digital imaging technologies. Digital imaging technologies provide digital processing capabilities, such as image capture, image archive, image transfer, and image display that may be shared among users to the medical study. Digital imaging technologies further allow data that is associated with the digital processing operations to be captured and combined with the underlying digital imaging processing operations.

Accordingly, a need exists to leverage digital imaging technologies to increase accountability and improve feedback among users that participate in a medical study.

SUMMARY OF THE INVENTION

The present invention relates to systems, methods and computer-based software programs that provide a QA scorecard for users that participate in a radiology imaging study. The QA scorecard provides the framework for developing a comprehensive medical imaging QA program that defines objective benchmarks. One of ordinary skill in the art will readily recognize that this invention may be applied to other medical disciplines, as well as to non-medical disciplines.

According to one embodiment, the invention is directed to radiological-based medical studies using digital imaging technologies. The medical studies are performed by users that perform discrete tasks in an imaging study workflow sequence. According to one embodiment of the invention, users include clinicians, radiologists, technologists, administrators and patients, among other users. A typical workflow sequence includes imaging exam ordering, imaging exam scheduling, imaging exam acquisition, imaging exam processing, imaging exam archiving, imaging exam distribution, imaging exam display, imaging exam navigation, imaging exam interpretation, imaging exam reporting, communication and billing, and administration of the workflow sequence, among other sequences.

According to one embodiment of the invention, client computers, one or more servers, the imaging devices, one or more databases, and/or other components may be coupled via a wired media, a wireless media, or a combination of the foregoing to provided a unified data collection system.

According to one embodiment of the invention, the client computers may include any number of different types of client terminal devices, such as personal computers, laptops, smart terminals, personal digital assistants (PDAs), cell phones, portable processing devices that combine the functionality of one or more of the foregoing or other client terminal devices.

According to one embodiment, the client computer may include client computer agent modules that gather client computer monitoring data based on user actions that are performed. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer may include client computer agent modules that gather client computer monitoring data based on computer actions that are performed. According to one embodiment of the invention, the client computer agent modules also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment, the metrics module may analyze data that is associated with a defined list of quality assurance (QA) benchmarks to objectively evaluate administrators, quantify a relative success of service delivery and provide educational (data-driven) feedback in order to optimize performance, among other benefits. The QA metrics may be tied to economic incentives, such as a pay for performance (P4P) systems, to create financial rewards for those users that provide high levels of quality-oriented service deliverables.

According to one embodiment, a quantifiable list of pre-defined administrator performance parameters may be used by the program to measure overall performance of the administrator, such as patient safety; patient satisfaction; clinician satisfaction; professional standards; clinical outcomes; timeliness of service; reporting/communication; technology performance; utilization; and image/exam quality; among other pre-defined parameters. According to one embodiment of the invention, performance metrics may be calculated by the program from various pre-defined parameters. For example, regarding patient safety, QA metrics may be calculated based on contrast-related concerns, such as allergic reactions, nephrotoxicity, extravastion; informed consent; physical injury; radiation exposure; and pharmaceutical administration; among other factors.

According to one embodiment of the invention, performance metrics may be calculated by the program from various parameters, including completeness of data input, such as exam findings; utilization patterns, including economic outcomes, clinical outcomes, and/or medico-legal outcomes; a patient safety profile, such as requested use of ionizing radiation, contrast, invasive procedures; communication/reporting, including the availability of imaging data, the production of imaging data, and/or clinician consultations; timeliness, including time to review imaging results; feedback provided to the clinician and/or patient; participation in data collection and analysis, including outcomes analysis, reporting, and/or diagnostic accuracy; education and training, including imaging services and new technologies; peer review, including discretionary assessment of performance as it relates to imaging services and patient diagnosis/treatment, among other parameters.

According to one embodiment of the invention, the imaging devices may include any number of different types of imaging devices, such as magnetic resonance imaging (MRI) devices, computer tomograph (CT) imaging devices, angiograph imaging device, ultrasound imaging devices or other imaging devices.

According to one embodiment of the invention, the imaging devices may include, or be modified to include, imaging device agent modules. The imaging device agent modules may operate to provide data gathering and data exchange functionality. According to one embodiment, the invention may enable monitoring of actions that are performed on the imaging devices.

According to one embodiment of the invention, the imaging device agent modules may associate imaging device identifying information with actions that are performed on the imaging devices. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices.

According to one embodiment of the invention, databases or information sources include a Hospital Information System (HIS) 10, a Radiology Information System (RIS) 20, a Picture Archiving and Communication System (PACS) 30, an Electronic Medical Record (EMR), a patient specific imaging datasheet and/or other information sources.

According to one embodiment of the invention, the server may include a merging module that receives data from all devices that are networked to the server, including the client computers, the imaging devices, and/or databases or information sources. According to one embodiment of the invention, the received data may include at least client computer audit log data and/or image device audit log data. According to one embodiment, the merging module merges data that is captured during a medical examination, including user action data, client computer action data, imaging device action data, and other data.

According to one embodiment of the invention, the data that is collected during the imaging study may analyzed by a metrics module that performs prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module may automatically tally and record QA scores. The QA scores may be cross-referenced by the computer program to a number of independent variables including a user identifier, imaging modality, exam type, patient demographics, patient characteristics, patient body habitus, exposure parameters, image processing, exam location, equipment, day/time of exam for trending analysis, radiologist identification, referring clinician, clinical indication, among other variables.

According to one embodiment of the invention, a standard tag may be created by the program within the various informational sources to identify individual QA data parameters. The communication module may extract the parameters from the information sources to calculate metrics and generate a QA score for the radiologist.

According to one embodiment of the invention, the QA metrics module may analyze various parameters to calculate a QA score for the administrator. According to one embodiment, the time-stamped data is a component part of objective data analysis. Imaging departments may utilize a program to record individual time-stamped data throughout the course of the imaging cycle, from the time an imaging exam is electronically ordered to the time the imaging report issued and reviewed. This is time-stamped data may be recorded into a QA database for subsequent analysis.

According to one embodiment, in order to optimize safety concerns and record/track cumulative data, the QA scorecard program provides patient safety data at any location where the patient is seeking and/or receiving medical imaging services. By storing the QA Scorecard data within a universal EMR, this data is made accessible to appropriate healthcare providers at any location.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to systems, methods, and computer-based software programs for generating quality assurance (QA) metrics, or scorecards, for administrators that participate in radiological-based medical studies.

Radiological-based medical studies of the present invention are conducted using digital imaging technologies. The medical studies are performed by many users that perform discrete tasks in an imaging study workflow sequence. Typically, the workflow sequence is initiated by a clinician, such as a family practice physician, that examines a patient and orders an imaging examination. The clinician's staff contacts an imaging center and schedules the imaging examination. At the imaging center, a technologist operates one or more imaging devices to acquire patient images. In some cases, the number of patient images taken may total several hundred or several thousand images. During the image acquisition operation, the technologist may process the images, including applying algorithms to the raw imaging data in order to enhance selected image features, reconstructing the raw image data in different ways to optimize imaging views, and/or performing other image processing. Upon completion of the imaging examination, the patient may be discharged from the imaging facility and the images may be locally stored. Generally, imaging administrators periodically obtain the images from the local storage devices and archive the images in a database, such as a Picture Archival Retrieval System (PACS) and/or other imaging databases. The images may be archived and retrieved based on selected criteria, including patient name, patient reference number, patient identifier, physician identifier, and/or other selected criteria.

After the images are archived, the images may be distributed to one or more specialists, such as a radiologist. Alternatively, a message may be communicated to one or more specialists advising the specialists that the images are available and providing instructions for accessing the archived images from the PACS or other imaging databases. The radiologist may access the PACS or other imaging databases and may perform image display and image navigation functions. The radiologist interprets the images and may access decision support tools or other interpretation tools during the image interpretation process. Following the image interpretation, the radiologist may generate a report and/or otherwise communicate the image study results to the referring clinician, among others. Upon completion of the imaging process, the radiologist, an administrator, and/or other service provider may perform billing operations. Additionally, an administrator may be tasked with defining the lines of responsibility for the participants of the imaging exam and for developing a comprehensive program that ensures appropriate levels of quality, while balancing economics, service deliverables and productivity. One of ordinary skill in the art will readily appreciate that the imaging study workflow sequence may include other operations.

Figure 1:
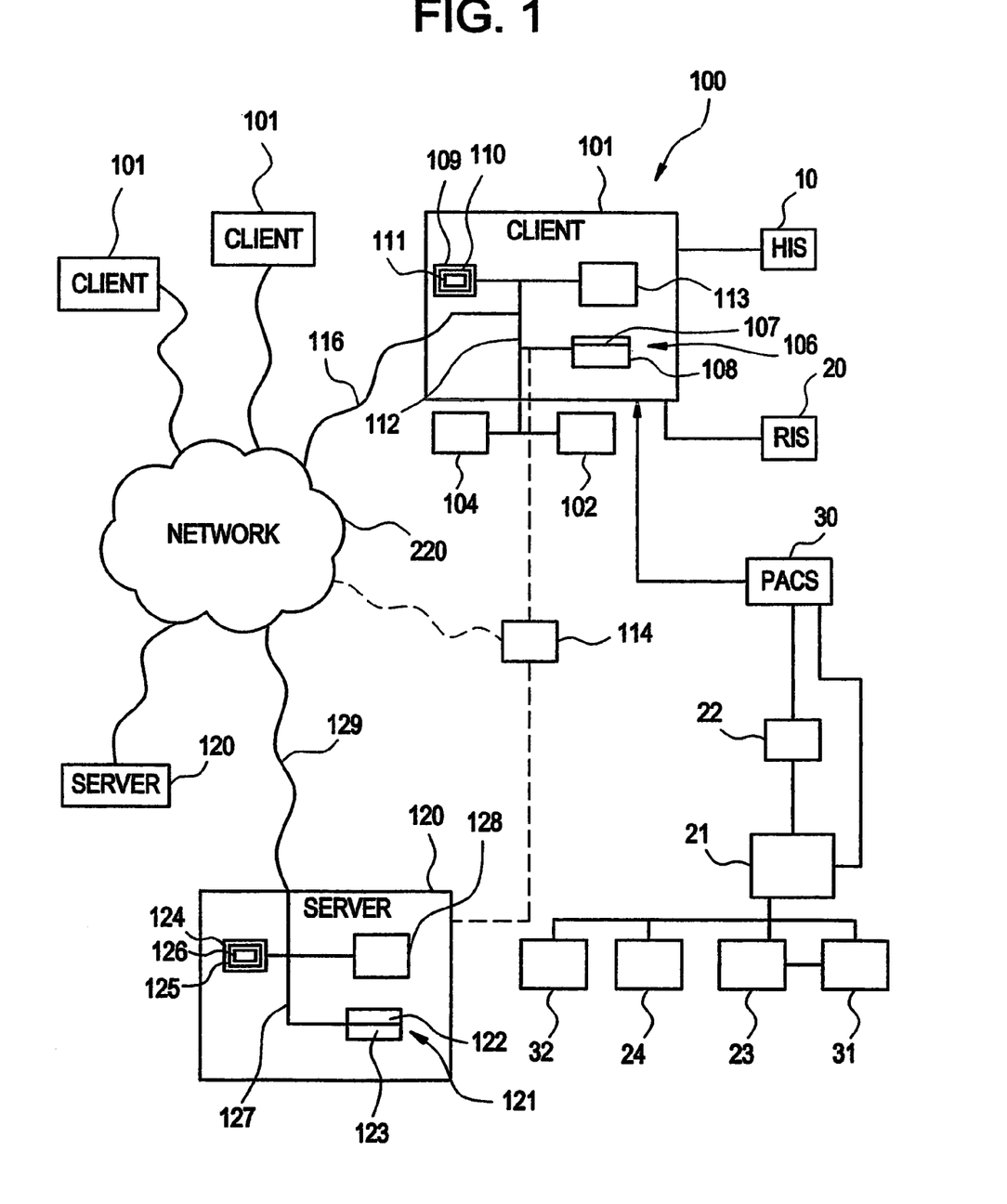
FIG. 1 illustrates a schematic diagram of a quality assurance scorecard system for radiology, according to one embodiment of the present invention.

According to one embodiment of the invention illustrated in FIG. 1, medical (radiological) applications may be implemented using the QA scorecard system 100. The QA scorecard system 100 is designed to interface with existing information systems such as a Hospital Information System (HIS) 10, a Radiology Information System (RIS) 20, a radiographic device 21 and/or other information systems that may access a computed radiography (CR) cassette or direct radiography (DR) system, a CR/DR plate reader 22, a Picture Archiving and Communication System (PACS) 30, and/or other systems. The QA scorecard system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the QA scorecard system 100 of the present invention and the information systems, such as the HIS 10, RIS 20, radiographic device 21, CR/DR plate reader 22, and PACS 30, etc., may be enabled to allow the QA scorecard system 100 to retrieve and/or provide information from/to these systems. According to one embodiment of the invention, bi-directional communication between the QA scorecard system 100 of the present invention and the information systems allows the QA scorecard system 100 to update information that is stored on the information systems. According to one embodiment of the invention, bi-directional communication between the QA scorecard system 100 of the present invention and the information systems allows the QA scorecard system 100 to generate desired reports and/or other information.

The QA scorecard system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the QA scorecard system 100 may include separate programs 110 having code that performs desired operations. According to one embodiment of the invention, the program 110 that runs the QA scorecard system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, QA scorecard system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

Figure 2:
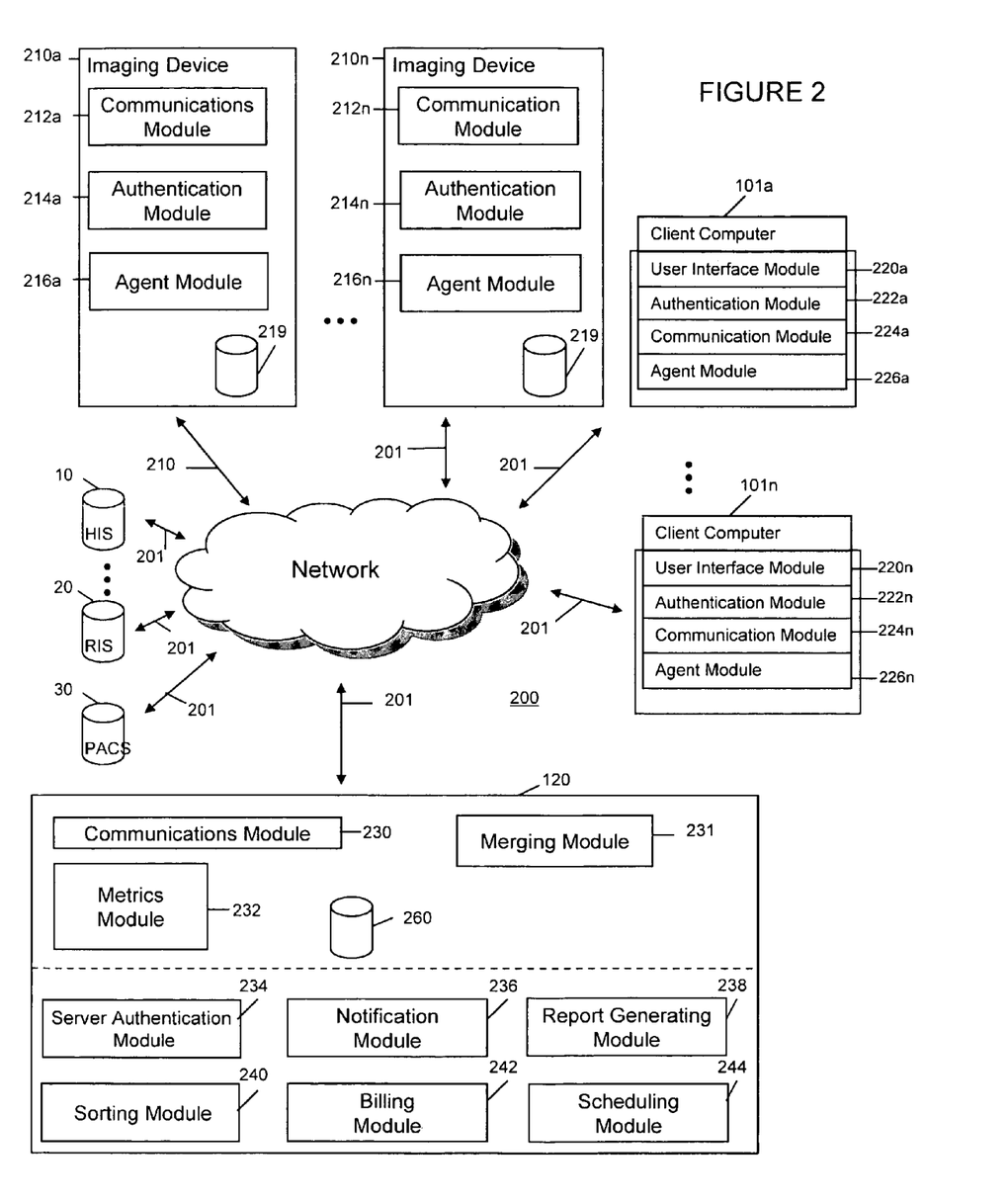
FIG. 2 illustrates a schematic diagram of a quality assurance scorecard system for radiology, according to another embodiment of the present invention.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

FIG. 2 illustrates the QA scorecard system 100 for providing QA assessments of clinicians that access a radiology system, according to one embodiment of the invention. According to one embodiment, the client computers 101a-101n (hereinafter client computers 101), one or more servers 120, the imaging devices 210a-210n (hereinafter imaging devices 210), one or more databases (HIS 10, RIS 20, PACS 30, etc.), and/or other components may be coupled via a wired media, a wireless media, or a combination of the foregoing. According to one embodiment of the invention, the client computers 101, the server 120, the imaging devices 210, and the databases may reside in one or more networks, such as an internet, an intranet, or a combination thereof.

According to one embodiment of the invention, the client computers 101 may include any number of different types of client terminal devices, such as personal computers, laptops, smart terminals, personal digital assistants (PDAs), cell phones, portable processing devices that combine the functionality of one or more of the foregoing or other client terminal devices.

According to another embodiment of the invention, the client computers 101 may include several components, including processors, RAM, a USB interface, a telephone interface, microphones, speakers, a stylus, a computer mouse, a wide area network interface, local area network interfaces, hard disk drives, wireless communication interfaces, DVD/CD readers/burners, a keyboard, a flat touch-screen display, a computer display, and/or other components. According to yet another embodiment of the invention, client computers 101 may include, or be modified to include, software that may operate to provide data gathering and data exchange functionality.

According to one embodiment of the invention, the client computers 101, the servers 120, and/or the imaging devices 210 may include several modules. The modular construction facilitates adding, deleting, updating and/or amending modules therein and/or features within modules. The client computer 101 may include various modules, including a user interface module 220, an authentication module 222, a communications module 224, an agent module 226, and/or other modules. The servers 120 may include various modules, including a server communication module 230, a merging module 231, a metrics module 232, a server authentication module 234, a notification module 236, a scheduling module 244 a report generating module 238, a sorting module 240, a billing module 242, and/or other modules. The imaging devices 210 may include various modules, including a communications module 212, an authentication module 214, an agent module 216 and/or other modules, along with a local storage device 219. It should be readily understood that a greater or lesser number of modules might be used. One skilled in the art will readily appreciate that the invention may be implemented using individual modules, a single module that incorporates the features of two or more separately described modules, individual software programs, and/or a single software program.

According to one embodiment of the invention, the client computer 101 may communicate through a networking application. According to another embodiment, the user interface modules 220a-220n (hereinafter user interface modules 220) may support several interfaces including display screens, voice recognition systems, speakers, microphones, input buttons, and/or other interfaces. According to one embodiment of the invention, the user interface modules 220 may display the application on a user interface associated with the client computer 101. According to one embodiment of the invention, select functions may be implemented through the client computer 101 by positioning an indicator over selected icons and manipulating an input device 104, such as a stylus, a mouse, a keyboard, or other input devices.

With regard to user authentication, the authentication modules 222a-222n (hereinafter user authentication modules 222) may employ one of several different authentication schemes, as would be appreciated by those skilled in the art. According to one embodiment of the invention, the user authentication modules 222 may prompt users to input alphanumeric code or other identifying information. According to another embodiment of the invention, the user authentication modules 222 may prompt users to provide biometric information (i.e., a thumbprint through a fingerprint scanner) or other suitable identifying information. If the user is not identified, then the user may be invited to resubmit the requested identification information or to take other action.

According to one embodiment of the invention, the client computers 101 may include communication modules 224a-224n (hereinafter communication modules 224) for enabling the client computers 101 to communicate with systems, including other client computers, the servers 120, the imaging devices 210, the databases and/or other systems. The client computers 101 may communicate via communications media 201 such as, for example, any wired and/or wireless media. Communications between the client computers 101, the imaging devices 21, the servers 120, and the databases may occur substantially in real-time, when the devices are coupled to the network. According to one embodiment of the invention, the communications module 224 may communicate with the servers 120 to exchange data, wherein the data exchange may occur with or without user awareness of the data exchange.

According to an alternative embodiment of the invention, communications may be delayed for an amount of time if, for example, one or more client computers 101, the server 120, the imaging devices 210, and/or the databases are not coupled to the network. According to one embodiment of the invention, any requests that are submitted while devices are not coupled to the network may be stored and propagated from/to the offline client computer 101, the databases and/or the imaging devices 210 when the target devices are re-coupled to the network. One of ordinary skill in the art will appreciate that communications may be conducted in various ways and among various devices.

According to one embodiment of the invention, user authentication information and/or identification information may be forwarded to the servers 120 to perform various functions. According to another embodiment of the invention, the servers 120 may operate to coordinate communications between the applications that are associated with the client computers 101, the imaging devices 210, and/or the databases.

According to one embodiment of the invention, the client computers 101 may include, or be modified to include, client computer agent modules 226a-226n (hereinafter client computer agent modules 226). The client computer agent modules 226 may operate to provide data gathering and data exchange functionality. According to one embodiment, the invention may enable monitoring of actions that are performed on the client computers 101.

According to one embodiment of the invention, the client computer agent modules 226 may associate client computer identifying information with actions that are performed on the corresponding client computers 101. According to one embodiment of the invention, data monitoring features may be employed to generate client computer audit logs. According to one embodiment of the invention, client computer audit logs may be produced to reconstruct actions, such as user actions, computer actions, and/or other actions that are performed on (or by) the client computers 101.

According to one embodiment, the client computer agent modules 226 may gather client computer monitoring data based on user actions performed, such as user login information; data files and databases that are accessed; information that is requested, including patient names/identifiers, exam results; information that is retrieved; client computer access information, including user information, time of access, time of exit, etc.; the application(s) that are used; information that is obtained from the server 120, including time of access, patient identifiers, volume of data retrieved, etc.; information that is obtained from the imaging devices 210, including time of access, patient identifiers, volume of data retrieved, etc.; information that is processed at the client computer 101, including time stamp information; and other user action data. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer agent modules 226 may gather client computer monitoring data based on computer actions performed, such as when data is exchanged; the type of input device used; whether reports are printed; when data is saved; an Internet Protocol (IP) address of devices that are communicated with; a location of data storage/retrieval; etc.; and/or other computer action data. According to one embodiment of the invention, the client computer agent modules 226 also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment of the invention, the server 120 may include a server authentication module 234 that receives authentication information that is entered into a corresponding client computer 101 via the authentication modules 222. The server authentication module 234 may compare the identifying information with existing records and operate as a gatekeeper to the QA scorecard system 100. If the user is determined to be a registered user, the authentication module 234 may attempt to authenticate the registered user by matching the entered authentication information with access information that exists on the servers 120. If the user is not authenticated, then the user may be invited to resubmit the requested identifying information or take other action. If the user is authenticated, then the servers 120 may perform other processing. For example, the client computers 101 may receive information from the servers 120 and/or from another authenticated client computers.

According to one embodiment of the invention, the imaging devices 210 may include any number of different types of imaging devices, such as magnetic resonance imaging (MRI) devices, computer tomograph (CT) imaging devices, angiograph imaging device, ultrasound imaging devices or other imaging devices. According to another embodiment of the invention, the imaging devices 210 may include several components such as processors, databases 219a-219n (hereinafter databases 219), RAM, a USB interface, a telephone interface, microphones, speakers, a stylus, a computer mouse, a wide area network interface, local area network interfaces, hard disk drives, wireless communication interfaces, a keyboard, a flat touch-screen display, a computer display, and/or other components.

According to one embodiment of the invention, the imaging devices 210 may include, or be modified to include, imaging device agent modules 216a-216n (hereinafter imaging device agent modules 216). The imaging device agent modules 216 may operate to provide data gathering and data exchange functionality. According to one embodiment, the invention may enable monitoring of actions that are performed on the imaging devices 210.

According to one embodiment of the invention, the imaging device agent modules 216 may associate imaging device identifying information with actions that are performed on the imaging devices 210. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices 210.

According to one embodiment, the imaging device agent modules 216 may gather image device monitoring data based on user actions performed, such as user login information; imaging modalities; parameters that are selected to perform the imaging modalities, including motion information, positioning information, exposure information, artifact information, collimation information; number of times an imaging exam is performed; data files and databases that are accessed; information that is requested, including patient names/identifiers; information that is retrieved; imaging device access information, including user information, time of access, time of exit, etc.; information that is stored to the server 120, including time of storage, patient identifiers, volume of data stored, etc.; information that was obtained from the imaging devices 210, including time of access, patient identifiers, volume of data stored, etc.; information that was processed at the imaging device 210, including time stamp information; and other user action data.

According to one embodiment, the imaging device agent modules 216 may gather imaging device monitoring data based on imaging device actions performed, such as when data is exchanged; the type of input device used; whether reports are printed; when data was saved; an Internet Protocol (IP) address of devices that were communicated with; a location of data storage/retrieval; imaging device parameter adjustments; and other imaging device data. According to one embodiment of the invention, the imaging device agent modules 216 also may gather imaging device specification data, such as resolution data, IP address data, processing speed data, and other imaging device specification data. According to one embodiment of the invention, the imaging device monitoring data and/or imaging device specification data may be stored in database 219. According to one embodiment of the invention, the imaging device monitoring data and/or imaging device specification data of the program 110 may be provided in real-time. According to another embodiment of the invention, the imaging device monitoring data and/or imaging device specification of the program 110 may be employed to calculate user QA metrics. The inventor has previously submitted an application describing an apparatus for automating QA in medical imaging, as described in U.S. patent application Ser. No. 11/412,884 filed on Apr. 28, 2006, the entire contents of which are hereby incorporated by reference.

According to one embodiment of the invention, the server 120 may include a merging module 231 that receives data from all devices that are networked to the server 120, including the client computers 101, the imaging devices 210, and/or databases. According to one embodiment of the invention, the received data may include at least client computer audit log data and/or image device audit log data. The merging module 231 may locally store the received data in a storage device 260 and/or may store the received data in an external storage device. The merging module 231 merges data that is captured during a medical examination, including user action data, client computer action data, imaging device action data, and other data.

According to one embodiment of the invention, the server 120 may include a sorting module 240 that enables sorting of the data, including the merged data. According to one embodiment of the invention, the sorting module 240 may sort the data based on various sorting criteria, including the chronology of data receipt, the type of device that originated the data, the type of technology used to obtain the data (e.g. CT, MRI, sonogram, etc.), the type of institution in which a data was obtained, the type of professional that obtained the data (i.e., radiologist, technologist, etc.), the user that is associated with the data, the patient that is associated with the data, demographic information, patient population information, the workflow sequence in which the data was captured, the severity of exam results, and/or other sorting criteria. According to one embodiment of the invention, the sorted data may enable tracking, reconstruction, reporting and/or monitoring of actions that are performed during medical examinations. According to one embodiment of the invention, the criteria associated with medical examinations may be used by the program to calculate QA scorecard metrics.

According to one embodiment of the invention, the server 120 may include a communications module 230 that communicates with the client computer 101, imaging devices 210 and/or databases to obtain information regarding the status of the imaging study along a defined workflow sequence. According to one embodiment of the invention, a defined workflow sequence includes various operations, such as image exam ordering, image exam scheduling, image exam acquisition, image processing, image archiving, image navigation, image interpretation, image exam reporting, image exam communication, and/or image exam billing. According to one embodiment of the invention, the communications module 230 provides the status of the imaging study workflow sequence including identifying the current user that is responsible for the image study, a completion percentage of the current stage of the imaging study, and/or other status information. According to one embodiment of the invention, the status of the imaging study workflow may be communicated to users in real-time and/or stored. According to one embodiment of the invention, parameters may be derived from the status of the imaging study workflow sequence by the program to generate a QA scorecard for the various users.

According to one embodiment of the invention, the server 120 may include a report generating module 238 that generates reports based on the occurrence of pre-defined events, including a periodic query of the status of the imaging study, an interpretation that is forwarded by the radiologist, a clinical finding that is submitted by the clinician, and/or the occurrence of other pre-defined events.

According to one embodiment of the invention, the server 120 may include a billing module 242. According to one embodiment, the billing module 242 performs billing functions following completion of the reporting/communication process. The billing module 242 may analyze metrics to assess operational efficiency and accuracy of charges billed and to calculate any additional expenses that occur due to limitations in reporting by users, such as radiologists. According to one embodiment, the additional expenses may take a number of forms and may result from uncertainty and equivocation within the radiology report or radiologist recommendations for additional imaging exams, consultations, and procedures (e.g. biopsy). The billing module 242 may correlate imaging costs with quality of service deliverables, such as diagnostic accuracy and clinical outcomes.

According to one embodiment of the invention, the server 120 may include a scheduling module 244 that enables electronic scheduling, including image exam scheduling. According to one embodiment, the scheduling module 244 may include bi-directional electronic scheduling that provides real-time tracking features to update parties of scheduling changes. The scheduling module 244 may communicate with the communication module 230 and/or the notification module 236, among other modules, to communicate the status of an appointment to users in real-time and/or stored.

According to one embodiment of the invention, the server 120 may include a notification module 236 that generates notifications and/or alerts based on the completion of reports, scheduling or the occurrence of predefined events. The notifications may be triggered by the release of items, such as status information, completion of an imaging report, changes to appointments, and/or other items. The notification module 236 may include monitoring features and/or confirmation features that track and record events, including the date and time that a notification is sent, the date and time that a notification is delivered, the date and time that a notification is opened, such as by return of an acknowledge receipt message, among other events. According to one embodiment, the notification module 236 may generate and forward notifications and/or alerts to client computers 101 and/or mobile devices, using known communication techniques including electronic mail messages, voice messages, telephone messages, text messages, instant messages, facsimile, and/or other communication techniques.

According to one embodiment of the invention, variables that are determined to have a deficiency during the imaging study process and that exceed a pre-determined QA standard threshold may trigger the computer program 110 to produce a notification and/or alert through the notification module 236 that may be instantaneously sent to users, via one or more communications techniques, alerting users as to the specific type of deficiency and requirement for correction.

According to one embodiment of the invention, a minimal amount of the data that is processed at the servers 120 may be stored in storage device 260 by the program 110. In other words, the servers 120 may perform data gathering and/or document generating functions and may thereafter purge all or portions of the retrieved data according to specified criteria. As a result, according to one embodiment, the program 110 may minimize security risks associated with exposing any confidential medical records to unauthorized parties at the servers 120. According to another embodiment of the invention, the retrieved data may be stored at the servers 120 by the program 110 for a predetermined amount of time before being purged. According to yet another embodiment of the invention, public record information, non-confidential retrieved data and/or tracking information, such as client computer log files and/or image device log files may be stored in storage device 260 by the program 110.

According to one embodiment of the invention, the metrics module 232 may receive objective scores, such as a Likert scale of 1-4, to quantify user performance. For example, a score of 1 may be considered "non-diagnostic". This means little or no clinically useful (diagnostic) information is contained within the image study. Since the available information obtained during the examination of the patient does not answer the primary clinical question (i.e., indication for the study), then by definition this requires that the imaging exam be repeated for appropriate diagnosis.

A score of 2 may be considered "limited". This means that the information obtained during the image study is less than expected for a typical examination of this type. However, the information contained within the image study is sufficient to answer the primary clinical question. A requirement that this exam be repeated is not absolute, but is preferred, in order to garner maximal diagnostic value.

A score of 3 may be considered "diagnostic". This means that the information obtained during the image study is representative of the broad spectrum of comparable images, allowing for the patient's clinical status and compliance. Both the primary clinical question posed, as well as ancillary information, can be garnered from the image for appropriate diagnosis.

A score of 4 may be considered "exemplary". This means that the information obtained during the image study and overall image quality serves as an example that should be emulated as the "ideal" for that specific imaging study and patient population.

According to one embodiment of the invention, the data that is collected during the imaging study may analyzed by a metrics module 232 for performing prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module 232 may automatically tally and record QA scores in a selected database. The QA scores may be cross-referenced by the computer program 110 to a number of independent variables including a user identifier, imaging modality, exam type, patient demographics, patient characteristics, patient body habitus, exposure parameters, image processing, exam location, equipment, day/time of exam for trending analysis, radiologist identification, referring clinician, clinical indication, among other variables. According to one embodiment of the invention, the report generating module 238 may access the QA scores to display results from the metrics module 232. The reports may be accesses at any time by users, including the clinician, the radiologist, the technologist, and/or the department/hospital administrator to review individual and collective performance results. The trending analysis provided by this data can in turn be used for educational purposes, performance review, and new technology deployment.

According to one embodiment, the metrics module 232 analyzes data that is associated with a defined list of quality assurance (QA) benchmarks to objectively evaluate administrators, quantify a relative success of service delivery and provide educational (data-driven) feedback in order to optimize performance, among other benefits. The QA metrics may be tied to economic incentives, such as a pay for performance (P4P) systems, to create financial rewards for those practitioners that provide high levels of quality-oriented service deliverables.

According to one embodiment, a quantifiable list of pre-defined administrator performance parameters may be used by the program 110 to measure overall performance of the administrator, such as patient safety; patient satisfaction; clinician satisfaction; professional standards; clinical outcomes; timeliness of service; reporting/communication; technology performance; utilization; and image/exam quality; among other pre-defined parameters. According to one embodiment of the invention, performance metrics may be calculated by the program 110 from various pre-defined parameters. For example, regarding patient safety, QA metrics may be calculated based on contrast-related concerns, such as allergic reactions, nephrotoxicity, extravastion; informed consent; physical injury; radiation exposure; and pharmaceutical administration; among other factors. According to one embodiment, patient safety factors may be recorded in an individual patient's electronic radiology folder, which may be associated with information sources, including the PACS 30, RIS 20, HIS 10, and EMR, among other information sources.

According to one embodiment of the invention, the pre-defined parameters (see the Table below) may be used to calculate the Administrative QA Scorecard. According to one embodiment of the invention, higher priority variables, such as clinical outcomes and patient safety, may have a proportionately higher numerical value than lower priority variables, such as technology performance. According to one embodiment of the invention, a cumulative QA score may be used as a multiplier of the standard technical reimbursement rate, so that a positive QA score of +18, would equate to a reimbursement fee of 118%, while a negative QA score of −14 would equate to a reimbursement rate of 86% of the standard fee. According to one embodiment of the invention, the scoring system may be equilibrated based on local and national norms and may include an institutional profile, specific type of exam, specific disease entity. According to one embodiment of the invention, the distribution profile for the collective group may be normalized to a bell-shaped curve, thereby maintaining no net increase or decrease in overall payments by third party payers. This quantifiable QA scoring system may also be used for large scale outcomes analysis

TABLE

| Predefined Parameters | Scoring System | Source of Data |
| --- | --- | --- |
| Patient Safety | −5 - - - +5 | RIS |
| Patient Satisfaction | −2 - - - +2 | Electronic Survey/RIS |
| Clinician Satisfaction | −2 - - - +2 | Electronic Survey/PACS |
| Professional Standards | −4 - - - +4 | RIS, PACS, EMR |
| Clinical Outcomes | −10 - - - +10 | EMR, PACS |
| Timeliness of Service | −3 - - - +3 | RIS, PACS, HIS |
| Reporting & Communication | −3 - - - +3 | PACS, EMR |
| Technology Performance | −1 - - - +1 | RIS, PACS, Digital Dashboard |
| Utilization | −2 - - - +2 | CPOE, RIS |
| Image/Exam Quality | −3 - - - +3 | RIS, PACS |

According to one embodiment of the invention, communication and reporting parameters may include, time from order entry to report completion; time from report completion to receipt by clinician; time from report receipt to actual review; specific components of the report reviewed by clinician; clinician time reviewing reporting data, such as document report open and report closing; clinician time components for individual report segments; report structure; report content; report organization; imaging links, including complete imaging file, key images, snapshot; ancillary data, including teaching files, NLM, review articles; communication; method of communication; acknowledgement of receipt of communication; bi-directional consultation; time to initiate treatment; tracking of follow-up recommendations; clinician satisfaction; subjective value; referral patterns; among other parameters. According to one embodiment, administrators may use reporting and communication data to analyze, for example, whether critical results are appropriately reported and communicated, whether system requirements are sufficient or need to be upgraded, whether report structures are acceptable and/or to perform other evaluations.

According to one embodiment of the invention, the communication module 230 may access a number of informational sources, including the electronic medical record (EMR); the computerized physician order entry system (CPOE); the hospital information systems (HIS) 10, the radiology information systems 20 (RIS); the picture archival and communication system (PACS) 30; subjective feedback from the radiologist, patient, and clinician peer group; and/or other informational sources, to obtain clinical performance parameters. According to one embodiment, standard tags may be created within the various informational sources to identify individual QA data parameters.

Figure 3:
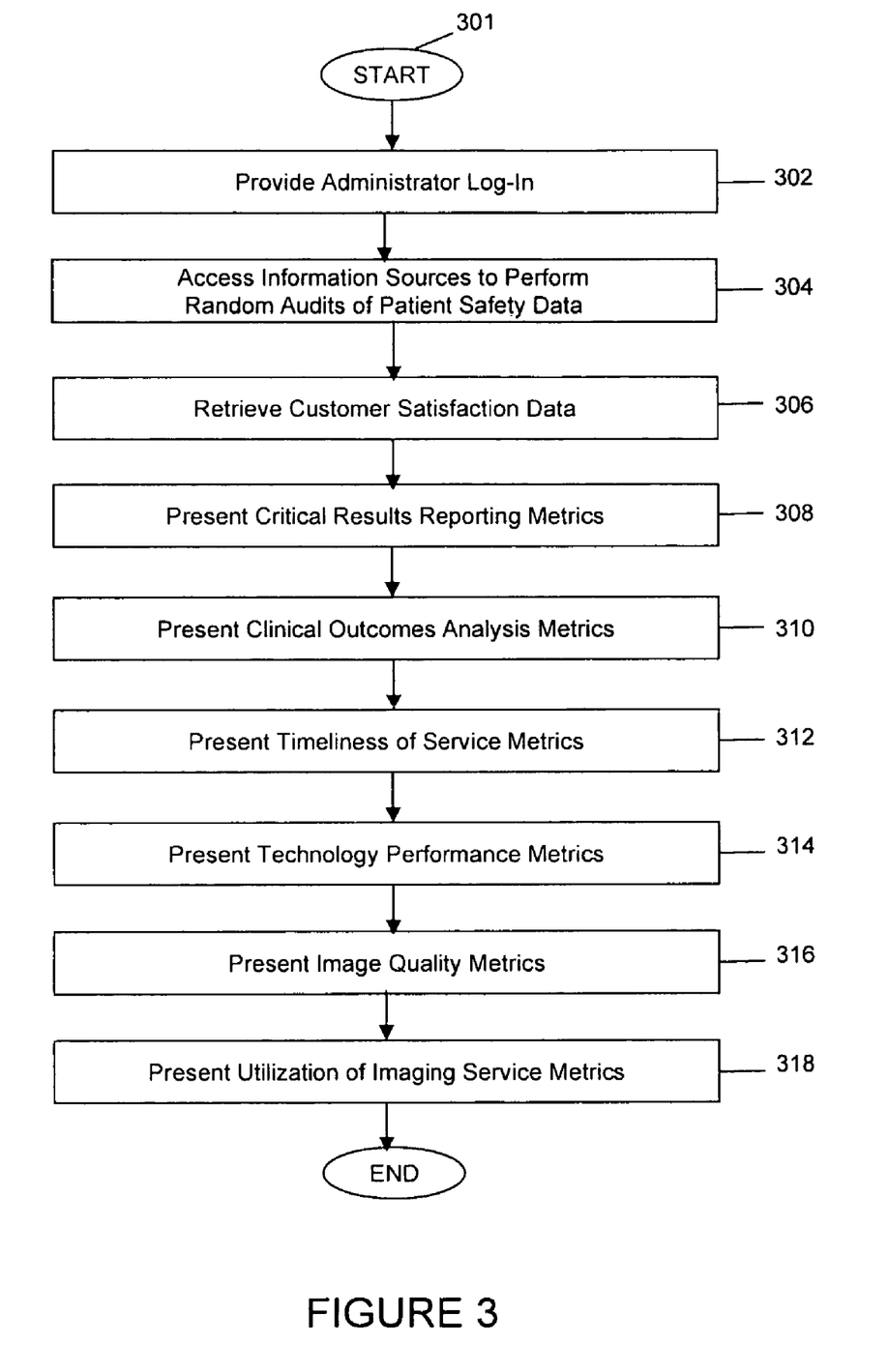
FIG. 3 illustrates a flow chart of a workflow sequence quality assurance program for imaging examinations from the perspective of an administrator, according to one embodiment of the present invention.

According to one embodiment of the invention illustrated in FIG. 3, the QA scorecard program 110 presents a welcome screen in operation, or step, 301. In operation 302, the QA scorecard program 110 displays a log-in screen and receives log-in criteria, such as a username and password. The QA scorecard program 110 compares the user log-in criteria against pre-stored log-in criteria for authorized users to determine if the user may gain access to the system. If the user log-in criteria is not approved, then the QA scorecard program 110 may notify the user of the registration failure and may return to the main log-in screen.

If the user log-in criteria is approved, then in operation 304, the QA scorecard program 110 may retrieve information from one or more information sources, including the electronic medical record (EMR), the hospital information system 10 (HIS), the radiology information system 20 (RIS), the PACS 30, among other information sources, to obtain information and/or records associated with patient safety in the administrator's domain. For example, the administrator may obtain QA metrics associated with contrast-related concerns, such as allergic reactions, nephrotoxicity, extravastion; informed consent; physical injury; radiation exposure; and pharmaceutical administration; among other factors. According to one embodiment, the QA metrics may be obtained based on several parameters including department, physician name, patient name, technologist name, facility, time period, and radiation exposure levels, among other parameters.

In operation 306, the QA scorecard program 110 may retrieve information from one or more information sources, including the electronic medical record (EMR), the hospital information system 10 (HIS), the radiology information system 20 (RIS), the PACS 30, among other information sources, to obtain information and/or records associated with customer satisfaction for customers within the administrator's domain. According to one embodiment, the QA scorecard program 110 may receive customer satisfaction data from kiosks that are provided throughout the imaging department and in the patient waiting/discharge areas. According to one embodiment, the QA scorecard program 110 may use the kiosks to present educational and discharge information to patients.

Regarding patient customer satisfaction data, the QA scorecard program 110 may query patients before they are discharged from the imaging examination. According to one embodiment, the QA scorecard program 110 may present a single pop-up menu that prompts the patient to provide an overall assessment of service, along with the individual assessments for the processes of scheduling, exam performance, attentiveness and courtesy of staff, and instructions for follow-up. For example, after completion of an imaging exam acquisition, the patient may be instructed to proceed to a discharge area. According to one embodiment, the patient may be presented with a client computer and may receive follow-up instructions from the QA scorecard program 110 as well as a multi-question electronic questionnaire requesting subjective feedback of their experience. According to one embodiment, the QA scorecard program 110 may present educational information, imaging alerts, and/or updates that may be forwarded to a specified client computer. According to one embodiment, the QA scorecard program 110 may record the patient responses into an information source. According to one embodiment, the QA scorecard program 110 may analyze the patient QA information and record the information in each patient's radiology folder, a comprehensive imaging QA database and/or other information database.

Regarding physician customer satisfaction data, the QA scorecard program 110 may present the physician with a pop-up menu that is attached to electronic imaging files and reports. According to one embodiment of the invention, the QA scorecard program 110 may randomly attach the pop-up menu to electronic imaging files and reports. According to one embodiment, the QA scorecard program 110 may present the physician with a client computer and may provide a multi-question electronic questionnaire requesting subjective feedback to assess the quality of images, report content and structure, and rate the communication and scheduling, among other factors. According to one embodiment, the QA scorecard program 110 may prompt the physician to provide feedback to specialists regarding patient-specific information that was not known or considered in the interpretation process.

According to one embodiment, the QA scorecard program 110 may record physician compliance, which may be made available to physician department heads in an attempt to improve the QA data collection process. According to one embodiment, the QA scorecard program 110 may record the physician responses into an information source and provide constructive feedback to the administrator for quality improvement. According to one embodiment, the QA scorecard program 110 may develop a physician profile that may assist imaging providers with the specific preferences of each physician, in an attempt to customize imaging content and service deliverables.

In operation 308, the QA scorecard program 110 may present critical results reporting metrics to administrators. According to one embodiment, the QA scorecard program 110 may track imaging reports that include clinical significance scores above a predefined threshold and/or imaging reports that include follow-up recommendations scores above a predefined threshold. According to one embodiment, the QA scorecard program 110 may track imaging reports for protocol adherence, compliance with patient care standards and testing standards, including timely processing, appropriate communication and/or other factors.

According to one embodiment of the invention, the QA scorecard program 110 may track imaging reports by timestamping and recording actions that are performed on the imaging reports, among other actions. According to one embodiment of the invention, the QA scorecard program 110 may track imaging reports by recording user identifies that access the imaging reports, among other information. According to one embodiment of the invention, the QA scorecard program 110 may store tracking information in the HIS 10, RIS 20, EMR or other information source and may associate the tracking data with a patient's profile.

In operation 310, the QA scorecard program 110 may present clinical outcome analysis metrics to administrators for assessing optimal allocations of resources, among providing other benefits. For example, the QA scorecard program 110 may be employed to present data that supports improved clinical outcomes based on use of a specific technology, a specific service, and/or a specific practitioner. According to one embodiment, the QA scorecard program 110 may weigh cost differential data with the improved clinical outcomes to provide more treatment options.

For example, the QA scorecard program 110 may compare various medical imaging technologies that are for managing suspected stroke patients to provide objective evidence of superior resources for diagnosing stroke patients. According to one embodiment, practitioners and/or administrators may present subjective evidence that MRI is more sensitive in the diagnosis of acute ischemia when compared with CT. However, this subjective evidence may be difficult to quantify based on inter-facility differences in exam protocols, differences in patient demographics, and differences in clinical presentations. According to one embodiment, the QA scorecard program 110 may provide large scale data to support this objective evidence.

According to one embodiment, the QA scorecard program 110 may prospectively collect, track, and analyze objective data to provide clinical measures that correlate with different imaging modalities for initial diagnosis and treatment. According to one embodiment, the QA scorecard program 110 may track parameters included in information sources, such as PACS 30, RIS 20, HIS 10, EMR or other information sources for patients that present with acute stroke symptoms. According to one embodiment of the invention, standard tags may be created by the program 110 within the various informational sources to identify individual QA data parameters.

According to one embodiment, the QA scorecard program 110 may access RIS 20 to track specific studies that were performed; the date and time of the exam order; exam completion; the technologist that performed the study; and the clinical indication for the exam, among other parameters. According to one embodiment, the QA scorecard program 110 may access PACS 30 to track the date and time the exam was reviewed, such as by the radiologist and/or referring clinician; the date and time the exam was interpreted; the exam protocol; the date and time the exam was reported, such as in preliminary and final formats; and communication of pertinent findings; among other parameters.

According to one embodiment, the QA scorecard program 110 may access the EMR to track clinical data parameters that are specific to the patient's presentation, diagnosis, treatment, and outcome, among other factors. According to one embodiment, the QA scorecard program 110 may access the history and physical exam prepared by the ER physician and/or the attending physicians; the neurologist consultation; the laboratory findings; the clinical tests; the progress notes, including tracking change in clinical status; treatment regimens, including surgical intervention, medical treatment, pharmaceutical administration; and discharge summary, which tracks morbidity and disposition; among other parameters.

According to one embodiment of the invention, the QA scorecard program 110 may access these parameters to perform outcome analysis and identify trends and relationships. According to one embodiment of the invention, the QA scorecard program 110 may perform outcome analysis on universal and standardized data that is collected and analyzed on patients within a given institution. According to one embodiment, administrators may use the QA scorecard program 110 to analyze objective evidence when practitioners advocate that specific technology provides more timely and accurate diagnosis.

According to one embodiment of the invention, the QA scorecard program 110 may determine the clinical impact of different imaging modalities in the diagnosis of acute stroke at a specific institution based on data stored in the information sources. According to one embodiment of the invention, the QA scorecard program 110 may access information sources to analyzed parameters, including a duration of symptoms at the time of clinical presentation; a specific neurological deficit on initial physical examination; imaging modality that is performed, including CT or MRI; protocols employed, with or without contrast administration; time from order entry to completion of imaging exam or exam time; time from patient presentation to documented preliminary results of the imaging study; diagnostic accuracy; confidence in diagnosis of imaging report; time from patient presentation to initiation of treatment; additional imaging studies required to obtain definitive diagnosis; length of hospital stay; prognosis; and residual neurological deficit at the time of discharge; among other parameters.

According to one embodiment of the invention, the QA scorecard program 110 may combine the imaging data and clinical data to obtain outcomes analysis relationships. According to one embodiment, the QA scorecard program 110 may perform outcome analysis based on timeliness, to define relationships between exam time, reporting time, time to initiate clinical treatment and eventual prognosis, among other time parameters. According to one embodiment, the QA scorecard program 110 may perform outcome analysis on the imaging exam to define relationships between the specific imaging modality and protocols on diagnostic accuracy and confidence in diagnosis, among other imaging exam parameters. According to one embodiment, the QA scorecard program 110 may perform outcome analysis on economic factors to define how different imaging and laboratory tests impact total cost of care, length of stay, and eventual prognosis, among other economic parameters. According to one embodiment, the QA scorecard program 110 may perform outcome analysis based on interpersonal variability to determine what degree of influence individuals have on diagnosis, treatment, and prognosis, among other interpersonal variability parameters. According to one embodiment, individuals may include the emergency room physician, the neurologist, the technologist, the radiologist, and/or other individuals.

In operation 312, the QA scorecard program 110 may present timeliness of service QA metrics. According to one embodiment, the QA scorecard program 110 may obtain timeliness of service metrics by compare timeliness of service data against customer satisfaction. According to one embodiment, the QA scorecard program 110 may store time-stamped data to calculate timeliness of service QA metrics. According to one embodiment, the QA scorecard program 110 may track parameters including exam ordering time; exam scheduling time; time of patient arrival; exam performance time, including begin and end times; time that completed exam is sent to PACS; exam review time; exam interpretation time; exam dictation time, including begin and end times; report completion time; report review time; time that clinical action is initiated; patient discharge time for inpatients, among other parameters.

According to one embodiment, the QA scorecard program 110 may derived several QA metrics from these time-stamped data elements to analyze efficiency of service deliverables. The QA metrics may include scheduling backlog, patient waiting time, length of stay for hospital inpatients, reporting time, treatment time, and total imaging cycle time. According to one embodiment, the QA scorecard program 110 may derive additional information include the users and technologies that were applied to review the stored data. According to one embodiment, the QA scorecard program 110 may provide information to the radiology and hospital administrators for analyzing how and/or when information is accessed, who is accessing the information, and the preferred method of communication. According to one embodiment, electronic communication pathways may be created by the program 110 to automate the communication process as defined by user profiles. According to one embodiment, automated communication may be mandated for high priority imaging exams, such as when the imaging exam is completed and when the corresponding report is completed. For example, clinicians may prefer text messaging, e-mail alerts, cell phone, faxing, and/or other communication methods. According to one embodiment, communication data may be recorded in the PACS, IS, and EMR. According to one embodiment, the QA scorecard program 110 may track and analyze workflow to identify delays and bottlenecks, which may be caused by humans or technology. According to one embodiment, the QA scorecard program 110 may track and analyze workflow on a regular basis or periodic basis and/or in real-time. In the event of critical delays, the QA scorecard program 110 may generate an alert to the IT department, hospital administrator, and/or radiology administrator, among others.

According to one embodiment, the QA scorecard program 110 may provide end-users, such as technologists, radiologists, clinicians, with real-time feedback and may provide alerts to become timelier in their actions. According to one embodiment, the QA scorecard program 110 may assist administrative decision-making as to appropriate IT resource allocation. According to one embodiment, the QA scorecard program 110 may be implemented to providing objective data for improving operational efficiency, workflow, and productivity in order to improve patient outcomes. According to one embodiment, the QA scorecard program 110 may make objective data available to the public to foster patient advocacy and inform customers as to the expected level of service.

In operation 314, the QA scorecard program 110 may present technology performance metrics associated with imaging devices, such as a CT scanner; information technologies, such as PACS; and supporting infrastructure, such as the network. According to one embodiment, the QA scorecard program 110 may track technology performance data in real-time. According to one embodiment, the QA scorecard program 110 may track technology performance to proactively identify bottlenecks and points of failure. According to one embodiment, the QA scorecard program 110 may track technology performance to routinely evaluate quality assurance and quality control. According to one embodiment, the QA scorecard program 110 may track technology performance to ensure technical specifications for quality are being maintained. According to one embodiment, the QA scorecard program 110 may employ both manual and automated testing to ensure appropriate calibration is performed and image quality is maintained.

According to one embodiment, administrators may use the QA scorecard program 110 to obtain cumulative data from the utilization analysis showing a need for a second MRI scanner, than this evidence may be provided to support a request for a second MRI during the next capital equipment cycle. In this regard, some states require certificates of need (CON) for certain types of advanced technologies (e.g. PET scanner) and this data provides an objective means to justify (or refute) requests for CON.

In operation 316, the QA scorecard program 110 may present image quality metrics based on subjective assessments performed by the radiologists and clinicians that interpret and act upon the imaging findings. According to one embodiment, the QA scorecard program 110 may present users with a pop-up QA menu. According to one embodiment, the QA scorecard program 110 may enable imaging studies to be assigned QA scores based on overall quality. According to one embodiment, the QA scorecard program 110 may store the assigned QA scores and associated parameters in a comprehensive QA database for future analysis. According to one embodiment, the QA scorecard program 110 may assign QA scores where "1" may correspond to non-diagnostic; "2" may correspond to limited; "3" may correspond to diagnostic; "4" may correspond to good; and "5" may correspond to exemplary. According to one embodiment, the QA scorecard program 110 may require additional descriptors of QA deficiency for scores in the ranges of 1 and 2.

According to one embodiment, administrators may use the QA scorecard program 110 to obtain QA metrics regarding technology and technologist performance, among other metrics, and may provide educational in-services and/or generate performance reviews based on the results. According to one embodiment, the QA scorecard program 110 may record and analyze radiologist and clinician QA preferences to automatically apply user-specific image processing in order to maximize perceived image quality.

In operation 318, the QA scorecard program 110 may present utilization of imaging services metrics. According to one embodiment, the QA scorecard program 110 may derive utilization of imaging service metrics from the computerized physician order entry (CPOE) based on parameters, such as the appropriateness of imaging exams requested, clinical data input, exam scheduling, and tracking of follow-up recommendations. According to one embodiment, administrators may use the utilization data from the QA scorecard program 110 to ensure that imaging services are being appropriately utilized. According to one embodiment, administrators may use the utilization data from the QA scorecard program 110 to ensure that the combined clinical and imaging input/output data is consistent, reproducible, and accurate.

According to one embodiment, the QA scorecard program 110 may interface with the CPOE application, which a clinician uses to initiate an exam order. The QA scorecard program 110 may receive data that includes all pertinent clinical data elements that are related to the diagnosis being evaluated. According to one embodiment of the invention, the data elements include past medical and surgical history; allergies, with particular emphasis directed to contrast media used in medical imaging; risk factors, including family history and tumor markers; non-imaging data, including laboratory, clinical testing, pathology; clinical indication and presumptive diagnosis, which prompted the ordered imaging exam; findings on physical examination; historical imaging data, including outside imaging exams and findings; and/or other data elements.

According to one embodiment, the QA scorecard program 110 may access clinical imaging variables to obtain exam order appropriateness. Exam order appropriateness is determined using a quantitative analysis that evaluates the clinical efficacy of the image exam ordered, based on an evaluation of the data elements associated with the examination request. According to one embodiment of the invention, the QA scorecard program 110 may objectively track the exam order appropriateness using pre-defined appropriateness criteria, such as linking clinical and historical data with different types of imaging exams. For example, if a clinician orders a chest CT to evaluate for lung cancer without first ordering a chest radiograph, the CPOE system may require the less expensive screening study (radiograph) to be performed before performing a more expensive CT. If, for example, the patient is being evaluated for kidney stones (urolithiasis) and has a past history of allergic reaction to intravenous contrast dye, the CPOE system will recommend a non-contrast CT or ultrasound (US) in lieu of an intravenous pyelogram (IVP), which requires contrast.

According to one embodiment of the invention, availability is a factor of exam appropriateness and may be defined as the ability to communicate in a timely fashion (i.e. accessibility). For example, availability may be a combined measure of the time requirements to document receipt of data and confirm a response.

According to one embodiment of the invention, willingness is a factor of exam appropriateness and may be defined as a degree with which an individual modified the imaging requisitions in accordance with appropriateness criteria data and recommendations of departmental staff. While there are situations where the clinician may insist on following a prescribed order, trending analysis may be performed by the program 110 to demonstrate outliers, in terms of those clinicians that consistently over-ride standard guidelines.

The appropriateness criteria are designed to take into account a multitude of clinical and imaging variables and provide objective feedback data by the program 110 to the ordering clinician in order to maximize patient safety, cost, and diagnostic accuracy. According to one embodiment of the invention, the metrics module 232 generates a QA score based on an evaluation of the appropriateness data.

According to one embodiment of the invention, another component of exam appropriateness may be the routine ordering of preventative screening imaging exams (e.g. screening mammography), in accordance with community standards and patient/family risk factors. As genetic markers become an integral part of the patient clinical profile, these preventative screening studies will take on greater importance in disease prevention and will also become an important component in the assessment of exam appropriateness.

According to one embodiment of the invention, the QA scorecard program 110 may provide trend analysis of medical imaging utilization. The trend analysis may be presented on an individual patient and patient group basis, with patient groups classified according to demographics, medical histories, and clinical profiles. According to one embodiment of the invention, the QA scorecard program 110 may present trend analysis to identify specific trends in imaging utilization patterns. Since patient, institution, and clinical indication are unique, they should be taken in the overall context of multiple data points.

According to one embodiment of the invention, the QA scorecard program 110 may present utilization data trends that are correlated with local, regional, and national norms. The QA scorecard program 110 may present utilization patterns in categories including, preventative medicine, diagnosis, treatment, and disease surveillance, among other categories.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of generating a quality assurance scorecard comprising:

providing a patient satisfaction questionnaire to a patient;

wherein said questionnaire requests that said patient provide an overall assessment of service;

wherein said assessment of service includes at least one of an individual assessment of a scheduling process, an exam performance, attentiveness and courtesy of staff, and instructions for follow-up;

receiving and storing said patient satisfaction data from said patient in at least one database of a computer system;

wherein said database includes at least one of an electronic medical record (EMR), a hospital information system (WS), a radiology information system (RIS), or PACS;

receiving imaging data and technology performance metrics associated with an imaging device;

storing in said database of said computer system, data related to patient safety information, said patient satisfaction data, critical results reporting metrics, clinical outcome analysis metrics, imaging data and clinical data outcomes analysis: timeliness analysis of patient service parameters; and said technology performance metrics associated with said imaging device:

wherein said patient safety information includes contrast-related adverse reactions;

informed consent; physical injury; radiation exposure; and pharmaceutical administration;

performing an analysis of said stored data and storing said analysis in said database of said computer system;

providing said analysis to a user;

wherein said user is one of a hospital administrator or a clinician;

generating, and storing in said database of said computer system, a quality assurance scorecard based on said analysis;

providing said clinician with a clinician questionnaire attached to at least one of electronic imaging files or reports;

wherein said clinician questionnaire includes requests for subjective feedback to assess at least one of image quality, report content and structure, or a rating of communication and scheduling; and wherein information from said clinician questionnaire is provided in said quality assurance scorecard to said hospital administrator.

2. The method according to claim 1, further comprising:

developing a profile for said clinician with specific preferences of each clinician, to customize imaging content and service deliverables.

3. The method according to claim 2, further comprising:

tracking at least one of imaging reports that include clinical significance scores above a predefined threshold or imaging reports that include follow-up recommendations scores above a predefined threshold;
wherein said imaging reports are tracked by recording user identities that access said imaging reports and associated with a patient's profile; and
wherein said imaging reports include protocol adherence, compliance with patient care standards and testing standards, timeliness, and appropriate communication.

4. A computer-implemented method of generating a quality assurance scorecard, comprising:
receiving imaging data and technology performance metrics associated with an imaging device;
storing in a database of a computer system, data related to obtaining and analyzing patient safety information, patient satisfaction information, critical results reporting metrics, clinical outcome analysis metrics, imaging data and clinical data outcomes analysis: timeliness analysis of patient service parameters; and said technology, performance metrics associated with an said imaging device, from at least one database;
performing an analysis of said stored data and storing said analysis in said database of said computer system;
providing said analysis to a user;
wherein said user is one of a hospital administrator or a clinician;
generating, and storing in said database of said computer system, a quality assurance scorecard based on said analysis;
presenting said clinical outcome analysis data to said user based on use of at least one of a specific technology, a specific service, or a specific user;
using said clinical outcome analysis data to assess at least an optimal allocation of resources; and
weighing a cost differential data with improved clinical outcomes to suggest additional treatment options.

5. The method according to claim 4, further comprising:
collecting, tracking, and analyzing objective data to provide clinical measures that correlate with different imaging modalities for initial diagnosis and treatment.

6. The method according to claim 5, further comprising:
accessing said database to track at least one of specific imaging examinations that were performed, including imaging examination order date and time, imaging examination completion, a technologist that performed said imaging examination, a clinical indication for said imaging examination, clinical data parameters that are specific to a patient's presentation, diagnosis, treatment, and outcome, a date and time said imaging examination was reviewed by said user, a date and time said examination was interpreted, a protocol for said imaging examination, a date and time an examination was reported, and a communication of pertinent findings to other users, for inclusion in said analysis.

7. The method according to claim 6, further comprising:
combining said imaging data and said clinical data to obtain at least one outcome analysis trend and relationship using standardized data collected and analyzed on patients within a selected institution;
wherein data elements related to a patient diagnosis are included in said clinical data, including at least one of past medical and surgical history, allergies, risk factors, non-imaging data, clinical indication and presumptive diagnosis, findings on physical examination, and historical imaging data; and
wherein said outcome analysis on said imaging data is used to define relationships between a specific imaging modality and protocols on diagnostic accuracy and confidence in diagnosis, and imaging examination parameters.

8. The method according to claim 7, wherein said outcome analysis is based on one of interpersonal variability or timeliness;
wherein timeliness includes relationships between imaging examination time, patient reporting time, time to initiate clinical treatment, and eventual prognosis; and
wherein timeliness of service data is achieved by comparing timeliness of service against said customer satisfaction data.

9. The method according to claim 8, further comprising:
obtaining QA metrics which are used in said analysis;
wherein said QA metrics are derived from time-stamped data elements to analyze efficiency of service deliverables, including scheduling backlog, patient waiting time, length of stay for hospital in-patients, patient reporting time, treatment time, and total imaging cycle time; and
providing information on said QA metrics to radiology and hospital administrators for analysis, including when said QA metrics information is accessed, the personnel accessing said QA metrics information, and a method of communication between users.

10. The method according to claim 9, further comprising:
tracking and analyzing workflow to identify delays and interruptions on a predetermined basis; and
alerting predetermined users when critical delays are identified;
wherein said alerts are forwarded on automated electronic communication pathways in accordance with user profiles.

11. The method according to claim 9, further comprising:
providing users with real-time feedback and alerts on said delays and interruptions to assist in administrative decision-making and appropriate resource allocation.

12. The method according to claim 11, further comprising:
tracking technology performance metrics associated with imaging devices in real-time to evaluate technology performance to maintain quality assurance and control, identify delays, and to maintain technical specifications; and
assigning quality assurance scores based on quality of said imaging examinations.

13. The method according to claim 12, further comprising:
enabling said user to obtain cumulative data from a utilization analysis for support of administrative requests.

14. The method according to claim 13, further comprising:
presenting image quality data based on subjective assessments to selected users.

15. The method according to claim 14, further comprising:
providing at least one of educational services or performance reviews of said user based on said QA metrics.

16. The method according to claim 15, further comprising:
deriving utilization of imaging service data from a computerized physician order entry (CPOE) based on at least one parameter related to said imaging examination;
wherein said parameter includes at least one of an appropriateness of said imaging exam, clinical data input, exam scheduling, and tracking of follow-up recommendations.

17. The method according to claim 16, further comprising:
enabling said user to use said utilization data to ensure that imaging services are being appropriately utilized, and that combined clinical and imaging input/output data is consistent, reproducible, and accurate.

18. The method according to claim 17, further comprising:
determining imaging examination order appropriateness using a quantitative analysis that evaluates a clinical efficacy of said imaging examination, based on an evaluation of said data elements associated with said imaging examination request;
wherein said imaging examination order appropriateness is determined using at least one pre-defined appropriateness criteria, including examination availability, routine ordering of preventative screenings, patient genetic markers, clinician willingness to modify imaging examination requests, and/or linking clinical and historical data with different types of imaging examinations; and
wherein said appropriateness is included in said quality assurance scorecard.

19. The method according to claim 18, further comprising:
providing trend analysis of medical imaging utilization on an individual or group basis;
identifying specific trends in imaging utilization patterns; and
correlating said utilization trends with local, regional, and national norms.

20. A computer system for generating an administrative quality assurance scorecard, comprising:
at least one memory containing at least one program containing instructions for executing the steps of:
providing a patient satisfaction questionnaire to a patient;
wherein said questionnaire requests that said patient provide an overall assessment of service;
wherein said assessment of service includes at least one of an individual assessment of a scheduling process, an exam performance, attentiveness and courtesy of staff, and instructions for follow-up;
receiving and storing said patient satisfaction data from said patient in at least one database of a computer system;
wherein said database includes at least one of an electronic medical record (EMR), a hospital information system (HIS), a radiology information system (RIS), or PACS;
receiving imaging data and technology performance metrics associated with an imaging device;
storing in said database of said computer system, data related to patient safety information, said patient satisfaction data, critical results reporting metrics, clinical outcome analysis metrics, imaging data and clinical data outcomes analysis; timeliness analysis of patient service parameters; and said technology performance metrics associated with said imaging device;
wherein said patient safety information includes contrast-related adverse reactions; informed consent; physical injury; radiation exposure; and pharmaceutical administration;
performing an analysis of said stored data and storing said analysis in said database of said computer system;
providing said analysis to a user;
wherein said user is one of a hospital administrator or a clinician;
generating, and storing in said database of said computer system, a quality assurance scorecard based on said analysis;
providing said clinician with a clinician questionnaire attached to at least one of electronic imaging files or reports;
wherein said clinician questionnaire includes requests for subjective feedback to assess at least one of image quality, report content and structure, or a rating of communication and scheduling; and
wherein information from said clinician questionnaire is provided in said quality assurance scorecard to said hospital administrator; and
a processor for running the program.

21. A non-transitory computer-readable medium containing instructions for executing a series of steps to generate a quality assurance scorecard on an administrator, comprising:
providing a patient satisfaction questionnaire to a patient;
wherein said questionnaire requests that said patient provide an overall assessment of service;
wherein said assessment of service includes at least one of an individual assessment of a scheduling process, an exam performance, attentiveness and courtesy of staff, and instructions for follow-up;
receiving and storing said patient satisfaction data from said patient in at least one database of a computer system;
wherein said database includes at least one of an electronic medical record (EMR), a hospital information system (HIS), a radiology information system (RIS), or PACS;
receiving imaging data and technology performance metrics associated with an imaging device;
storing in said database of said computer system, data related to patient safety information, said patient satisfaction data, critical results reporting metrics, clinical outcome analysis metrics, imaging data and clinical data outcomes analysis; timeliness analysis of patient service parameters; and said technology performance metrics associated with said imaging device;
wherein said patient safety information includes contrast-related adverse reactions; informed consent; physical injury: radiation exposure; and pharmaceutical administration;
performing an analysis of said stored data and storing said analysis in said database of said computer system;
providing said analysis to a user;
wherein said user is one of a hospital administrator or a clinician;
generating, and storing in said database of said computer system, a quality assurance scorecard based on said analysis;
providing said clinician with a clinician questionnaire attached to at least one of electronic imaging files or reports;
wherein said clinician questionnaire includes requests for subjective feedback to assess at least one of image quality, report content and structure, or a rating of communication and scheduling; and
wherein information from said clinician questionnaire is provided in said quality assurance scorecard to said hospital administrator.

22. A computer system for generating an administrative quality assurance scorecard, comprising:
at least one memory containing at least one program containing instructions for executing the steps of:
receiving imaging data and technology performance metrics associated with an imaging device;
storing in a database of a computer system, data related to obtaining and analyzing patient safety information, patient satisfaction information, critical results reporting metrics, clinical outcome analysis metrics, imaging data and clinical data outcomes analysis; timeliness analysis of patient service parameters; and said technology performance metrics associated with an said imaging device, from at least one database;

performing an analysis of said stored data and storing said analysis in said database of said computer system;

providing said analysis to a user;

wherein said user is one of a hospital administrator or a clinician;

generating, and storing in said database of said computer system, a quality assurance scorecard based on said analysis;

presenting said clinical outcome analysis data to said user based on use of at least one of a specific technology, a specific service, or a specific user;

using said clinical outcome analysis data to assess at least an optimal allocation of resources; and weighing a cost differential data with improved clinical outcomes to suggest additional treatment options; and a processor which runs the program.

23. A non-transitory computer-readable medium containing instructions for executing a series of steps to generate a quality assurance scorecard on an administrator, comprising:

receiving imaging data and technology performance metrics associated with an imaging device;

storing in a database of a computer system, data related to obtaining and analyzing patient safety information, patient satisfaction information, critical results reporting metrics, clinical outcome analysis metrics, imaging data and clinical data outcomes analysis; timeliness analysis of patient service parameters; and said technology performance metrics associated with an said imaging device, from at least one database;

performing an analysis of said stored data and storing said analysis in said database of said computer system;

providing said analysis to a user;

wherein said user is one of a hospital administrator or a clinician;

generating, and storing in said database of said computer system, a quality assurance scorecard based on said analysis;

presenting said clinical outcome analysis data to said user based on use of at least one of a specific technology, a specific service, or a specific user;

using said clinical outcome analysis data to assess at least an optimal allocation of resources; and weighing a cost differential data with improved clinical outcomes to suggest additional treatment options.

* * * * *